United States Patent [19]

Ryder et al.

[11] Patent Number: 5,639,599
[45] Date of Patent: Jun. 17, 1997

[54] AMPLIFICATION OF NUCLEIC ACIDS FROM MONONUCLEAR CELLS USING IRON COMPLEXING AND OTHER AGENTS

[75] Inventors: Thomas B. Ryder, Escondido; Daniel L. Kacian, San Diego, both of Calif.

[73] Assignee: Gen-Probe Incorporated, San Diego, Calif.

[21] Appl. No.: 254,310

[22] Filed: Jun. 6, 1994

Related U.S. Application Data

[63] Continuation-in-part of Ser. No. 895,587, Jun. 8, 1992, abandoned.

[51] Int. Cl.[6] .............................. C12Q 1/70; C12Q 1/68; C12P 19/34
[52] U.S. Cl. ........................... 435/5; 435/6; 435/91.2; 435/91.21
[58] Field of Search ..................... 435/5, 6, 91.2, 435/91.21, 810; 536/25.4, 25.41, 25.42

[56] References Cited

U.S. PATENT DOCUMENTS

| | | | |
|---|---|---|---|
| 3,852,424 | 12/1974 | Gaeumann et al. | 424/118 |
| 3,957,435 | 5/1976 | Adams et al. | 23/230 B |
| 4,683,202 | 7/1987 | Mullis | 435/91.2 |
| 4,767,708 | 8/1988 | Minkley, Jr. et al. | 435/194 |
| 4,863,964 | 9/1989 | Hedlund et al. | 514/575 |
| 5,284,940 | 2/1994 | Lin et al. | 536/25.4 |
| 5,399,491 | 3/1995 | Kacian et al. | 435/91.21 |

FOREIGN PATENT DOCUMENTS

| | | |
|---|---|---|
| 0300796 | 1/1989 | European Pat. Off. . |
| 0338591 | 10/1989 | European Pat. Off. . |
| 8902476 | 3/1989 | WIPO . |
| 9101384 | 2/1991 | WIPO . |
| 9303167 | 2/1993 | WIPO . |

OTHER PUBLICATIONS

Modak et al., *J. Biol. Chem.* 254(11), 4756–4759 (1979).
Aw et al, *Arch. Biochem. Biophys.* 283(1), 46–50 (1990).
Conti et al., *Boll. Ist. Sieroter.* 69(2), 431–435 (1990).
Arnold et al., "Assay Formats Involving Acridinium–Ester–Labeled DNA Probes," *Clinical Chemistry* 35:1588–1594 (1989).
Auld et al., "Zinc Reverse Transcriptases From Mammalian RNA Type C Viruses," *Biochemical and Biophysical Research Communications* 62:296–302 (1975).
Bignold, "Preparative techniques influencing sedimentation of erythrocytes through the Hypaque–Ficoll medium used in the one–step technique for separation of human polymorphonuclear leukocytes from whole blood," *J. Immun. Methods* 106:147–149 (1988).

(List continued on next page.)

*Primary Examiner*—Kenneth R. Horlick
*Attorney, Agent, or Firm*—Lyon & Lyon

[57] ABSTRACT

Method and kit for the preparation of nucleic acid, such as for amplification. The nucleic acid may be prepared by centrifuging a sample of whole cells, particularly mononuclear cells, with an appropriate centrifugation medium so as to separate desired cells from non-desired cells, then removing and lysing said desired cells. A complexing agent able to complex ferric ion may be added to the lysed cells. The nucleic acid associated with the lysed cells can be amplified, and the nucleic acid can also be screened for a certain nucleic acid sequence, such as a vital nucleic acid sequence.

129 Claims, 3 Drawing Sheets

OTHER PUBLICATIONS

Bottu, "The Effect of Quenchers on the Chemiluminescence of Luminol and Lucigenin" *J. Bioluminescence and Chemiluminescence* 3:59–65 (1989).

Boyum, (5 consecutive papers), *Scand. J. Clin. Lab. Invest.* 21 (Suppl. 97):9–109 (1968).

Buck et al., "Rapid Simple Method for Treating Clinical Specimens Containing *Mycobacterium tuberculosis* to Remove DNA for Polymerase Chain Reaction," *J. Clin. Microbiol.* 30:1331–1334 (1992).

Calam, "Specimen Processing Separator Gels: An Update," *J. Clin. Immunoassay* 11:86–90 (1988).

Champelovier and Seigneurin, "A Comparison of 3 Cell Separation Media: Application to the Enrichment for Immature Cells of the Granular Myeloid Line," *Biomedicine* 36:378–380 (1982).

Clouse et al., "Rapid Method for Purification of Human T Lymphocytes for Further Functional Studies," *J. Immun. Methods* 105:253–262 (1987).

deFranchis et al., "A Potent Inhibitor of Taq Polymerase Copurifies with Human DNA," *Nucleic Acids Research* 16:10355 (1988).

Fatino et al., "Micromethod for Rapid Separation of Lymphocyes from Peripheral Blood," *Annals of Clin. Lab. Science* 1:131–133 (1971).

Gust and Maskill, "Diagnostic tests for the human immunodeficiency virus," *Medical Journal of Australia* 151:57–58 (1989).

Guttridge, "Age Pigments and Free Radicals: Fluorescent Lipid Complexes Formed by the Iron–and Copper–Containing Proteins," *Biochemica et Biophysica Acta* 834:144–148 (1985).

HRI Research Incorporated brochure, "AmpPrep™," Oct. 1991.

Kain et al., "Determination of Genetic Variation with in Plasmodium Falciparum by Using Enzymatically Amplified DNA from Filter Paper Disks Impregnated with Whole Blood," *Journal of Clinical Microbiology*, 29:1171–1174 (1991).

Kawasaki, "Sample Preparation From Blood, Cells, and Oter Fluid," *PCR Protocols*, Innis, Gelfand and Sninsky eds. (Academic Press, Inc.:San Diego, 1990) pp. 146–148.

Kellog and Kwok, "Detection of Human Immunodeficiency Virus," *PCR Protocols*, Innis, Gelfand and Sninsky eds. (Academic Press, Inc:San Diego, 1990) pp. 337–343.

Martell et al, "Development of Iron Chelators for Cooley's Anemia," *Inorganic Chimica Acta* 138:215–230 (1987).

Michalski, "The Diagnosis of Human Immunodeficiency Virus Infection: Progress in Less Than Five Years," *Yale J. of Biol. and Med.* 62:93–102 (1989).

NYCOMED, "Density Gradient Media," (product brochure) published by NYCOMED AS, Pharma Division Diagnostica, Sandakervn 64, P.O. Box 4284 Torshov, N–0401 Oslo 4, Norway.

PERCOLL®, "Methodology and Applications Density Marker Beads for Calibration of Gradients of PERCOLL®," published by Pharmacia, Laboratory Separation Division, Uppsala, Sweden.

Prat and Turrens, "Ascorbate–and Hemoglobin–Dependent Brain Chemiluminescence," *Free Radical Biol. & Med.* 8:319–325 (1990).

Price and Glasser, "Neutrophil Collection Using Modified Fluid Gelatin," *Transfusion* 25:238–241 (1985).

Seal, "Silicone Flotation: A Simple Quantitative Method for the Isolation of Free–Floating Cancer Cells From the Blood," *Cancer* 3:590–595 (1959).

Sepracell–MN® Separation Manual, published by Sepratech Corporation, Oklahoma City, Oklahoma.

Slaby, "T7 DNA Polymerase is not a Zinc–Mettaloenzyme and the Polymerase and Exonuclease Activities are Inhibited by Zinc Ions," *Biochem. and Biophys. Res. Comm.* 122:1410–1417 (1984).

Van Wie and Hustvedt, "Particle Interaction Effects on Blood Cell Sedimentation and Separations," *Biorheology* 25:651–662 (1988).

Videla et al., "Antioxidant Capacity of Desferrioxamine in Biological Systems," *Biochem. Int'l.* 15:205–214 (1987).

Videla et al., "Antioxidant Capacity of Desferrioxamine and Ferrioxamine in the Chemically–initiated Lipid Peroxidation of Rat Erythrocyte Ghost Membranes" *Biochemistry International* 16:799–807 (1988).

Walker et al., "Isothermal *in vitro* amplification of DNA by a restriction enzyme/DNA polymerase system," *Proc. Natl. Acad. Sci. USA* 89:392–396 (1992).

Walsh, et al., "Chelex® 100 as a Medium for Simple Extraction of DNA for PCR–Based Typing from Forensic Material," *Biotechniques* 10:506–513 (1991).

Wolff, "The Separation of Cells and Subcellular Particles by Colloidal Silica Density Gradient Centrifugation," *Meth. Cell Biol.*, Prescott, D.M., ed. (Academic Press, NY: 1975) vol. 10, pp. 85–104.

Wu and Wu, "Zinc in DNA Replication and Transcription," *Ann. Rev. Nutr.* 7:251–272 (1987).

AMPLIFICATION OF NUCLEIC ACIDS FROM MONONUCLEAR CELLS USING IRON COMPLEXING AND OTHER AGENTS

This application is a continuation-in-part of Ryder et al., entitled "Preparation of Nucleic Acid from Mononuclear Cells," filed Jun. 8, 1992, and assigned U.S. Ser. No. 07/895,587, abandoned, hereby incorporated by reference herein.

BACKGROUND OF THE INVENTION

The field of the present invention is the preparation of nucleic acid for study, research and investigation.

It is common to require nucleic acid to be isolated and purified (i.e., prepared) from various tissues in order to detect the presence of a particular nucleic acid—for example, the presence of HIV-1 DNA or RNA in a blood cell of a human. For this purpose, the nucleic acid is generally extracted after extensive purification of appropriate blood cells, lysis of these cells and purification of the released nucleic acids to remove substances that might inhibit later analytical procedures. In particular, it is important to produce nucleic acid of a quality and purity to allow its amplification.

Two common methods which allow amplification of a specified sequence of nucleic acid (e.g., deoxyribonucleic acid (DNA) or ribonucleic acid (RNA)) are one termed the "polymerase chain reaction" (where two primers are used to synthesize nucleic acid lying between the regions where the primers hybridize), and one which uses RNAse H, reverse transcriptase and RNA polymerase. These methods are described respectively by Mullis et al., U.S. Pat. No. 4,683,202 and by Kacian et al., PCT/U.S. Ser. No. 90/03907 both hereby incorporated by reference herein.

SUMMARY OF THE INVENTION

The present invention is directed to methods and kits for the preparation of nucleic acid, and particularly for isolation of DNA or RNA from cells, such as mononuclear cells (e.g., T-lymphocytes and/or monocytes), for amplification of that nucleic acid. Such amplified nucleic acid may then be used for various purposes, including screening the nucleic acid for the presence of viral nucleic acid sequences, using a probe which is complementary to a selected nucleic acid sequence of the virus. It is also useful for detection of genetic anomalies or defects in the nucleic acid. Accordingly, the methods and kits are designed to allow rapid and easy preparation of nucleic acid without the need for extensive purification procedures.

Thus, in a first aspect, the present invention features a method for preparing nucleic acid from cells for amplification. A sample containing various cells (e.g., whole blood) and an appropriate centrifugation medium are centrifuged to cause a population of one cell type to gather in a discrete layer. This layer is separate and distinct from the remainder of the cells and detritus in the sample, except for a small amount of platelets and/or lipids or other low density components, or other soluble and suspended constituents. Surprisingly, the presence of platelets and other components does not prevent amplification of nucleic acid purified in this method.

Preferably, the population of cells includes mononuclear cells from whole blood. However, the cells may be cells other than mononuclear cells and/or may be derived from other sources, such as pleural fluid, synovial fluid, or an in vitro source of cells. The cells or sample of cells need only be available to be centrifuged for separation, or in a state to be lysed (as discussed below), and then effectively used in later reactions according to the present invention. The centrifugation medium may be isotonic and/or isopycnic to the cells, and is preferably of a density intermediate between that of the desired cells and of the other cells in the sample.

The cells are removed from the centrifugation composition, for example by suction using a pipette, and lysed. Such lysis makes the nucleic acid associated with the cells available for the amplification.

In preferred embodiments, the method includes adding a complexing agent that complexes with, and effectively removes, ferric ions ($Fe^{+++}$) from the solution before amplifying the nucleic acid. The presence of ferric ions interferes with certain enzymatic procedures, such as those used for nucleic acid amplification. The complexing agent is preferably selected so that it has greater affinity, e.g., at least four logs greater, for ferric ions than for ($Zn^{++}$), manganese ions ($Mn^{++}$) or magnesium ions ($Mg^{++}$), as these ions are beneficial and tend to facilitate these enzymatic reactions. Such an agent is the chelating agent deferoxamine (also known as desferrioxamine and desferrioxamine B).

In other preferred embodiments, a second or different complexing agent may be added that complexes with calcium ions ($Ca^{++}$), or other ions that interfere with an amplification reaction or other reactions performed with the lysate of the present invention. Calcium ions may also interfere with enzymatic reactions used in amplification procedures. The second complexing agent is most preferably selected so as to fail to complex with zinc ions or magnesium ions, or to have more affinity for undesirable ion species (such as $Fe^{+++}$ and $Ca^{++}$) than for desirable ion species (such as $Zn^{++}$, $Mn^{++}$, and $Mg^{++}$).

In yet more preferred embodiments, zinc ions, manganese ions or magnesium ions may be added to the solution to facilitate enzymatic reactions.

In a second related aspect, the invention features a method of amplifying nucleic acid in which the nucleic acid to be amplified is produced in a solution with ferric ions, and those ferric ions effectively removed from the mixture by use of a complexing agent such that amplification can occur. The solution may also contain calcium ions, which are preferably also removed from the solution by a complexing agent, so that amplification may occur.

In a third related aspect, the invention features a method for amplifying nucleic acid from whole cells. In the method, the whole cells are lysed prior to amplification by the use of a strong alkali such as KOH, NaOH or LiOH. Such a lysis also denatures any double stranded nucleic acid from the cells, thereby facilitating amplification. After lysis, a ferric ion complexing agent is preferably added to remove ferric ion from the suspension or composition.

Once the nucleic acid has been amplified, methods are known in the art for screening the amplified nucleic acid using known nucleic acid hybridization and detection techniques. For example, by using a nucleic acid probe complementary to a target sequence (which preferably includes the sequence targeted for amplification), hybridizing the probe to the target nucleic acid sequence, and detecting the complex of probe and target by well known methods, such as Southern or northern blots or by the homogeneous solution phase procedure ("HPA") described in Arnold et al, *Clin. Chem.*, 35: 1588 (1989), and PCT U.S. Ser. No. 88/02746, all of which are hereby incorporated by reference. By the use of such a probe detection method, it can be determined whether vital nucleic acid, such as that from HIV or hepatitis B virus (HBV), is associated with the nucleic acid present in the sample. Such a screening may also target any other sort of nucleic acid sequence, such as a genetic anomaly or defect. The use of such amplification procedures allows even a single copy of the targeted nucleic acid in the portion of the sample recovered after centrifugation to be detected using the present invention.

It is a further feature of the invention to provide a kit including apparatus, media and agents necessary to conduct the above described inventive method. For example, the kit may include a supply of the centrifugation medium (and an osmotic agent, if necessary), a supply of a lysing agent sufficient to lyse the cells from the sample, and a supply of the amplification materials sufficient to amplify the nucleic acid from the cells. Such a kit may also include a ferric ion and/or calcium ion complexing agent, and, a supply of the probe for a desired nucleic acid target, or a known genetic anomaly.

Other features and advantages of the invention will be apparent from the following description of the preferred embodiments, and from the claims.

DESCRIPTION OF THE PREFERRED EMBODIMENTS

The claimed method features a series of steps for the collection, isolation, preparation, amplification and screening of nucleic acid, preferably from mononuclear cells, and a combination of apparatus, media and agents to effectuate such a method. The various steps, apparatus, media and agents are discussed generally above, and examples are now provided.

Obtaining a Sample of Cells

A sample of cells may be provided from any suitable source, such as from whole blood, or from synovial fluid, pleural fluid, or other fluids containing cells of interest. Preferably, the sample comprises mononuclear cells in anti-coagulant treated whole blood, which may be obtained from any animal, including a human being. The blood may be pretreated if desired, e.g., to remove red blood cells and/or fibrin, provided that the mononuclear cells (or other cells of interest) remain in the fluid. Other blood fractions or any other fluids containing cells of interest can be used.

The blood, or other source of a sample of cells, may be obtained using any available method, including those known in the art. The sample can be obtained and stored, and even subjected to centrifugation, in the same device. If the sample is blood, it may be desirable to treat the sample with an anti-coagulant, such as EDTA or Heparin, so that the blood does not coagulate prior to performance of the rest of the method, or during use of the rest of the materials and apparatus in the kit.

Preparing the Composition

It is useful to make a composition of the sample and a centrifugation medium such that, upon centrifugation, the mononuclear cells gather in a discrete band. By "gather in a discrete band," it is meant that the desired cells effectively move through the composition to a particular density level, and are sufficiently separated from the remainder of the cells and other detritus in the composition that later enzyme reactions, such as amplification, can proceed. Such centrifugation media are known in the art. See, e.g., Percoll Methodology and Applications Density Marker Beads for Calibration of Gradients of PERCOLL®, published by Pharmacia, Laboratory Separation Division, Uppsala, Sweden; Sepracell-MN® Separation Manual, published by Sepratech Corp., Oklahoma City, Okla.; NYCOMED® Density Gradient Media, published by Nycomed, Oslo, Norway. The centrifugation medium may be isotonic to the cells of the sample, and may also be generally isopycnic to the cells from the sample or, preferably, of a density intermediate the cell population of interest and other cell populations in the sample. The centrifugation medium and the sample of cells may be mixed prior to centrifugation such that there is no density gradient prior to centrifugation. By "isopycnic," it is meant that the centrifugation medium is approximately the same density as the cells in the sample, such that, upon centrifugation, desired cells from the sample will separate from the remainder of the mixture, which remainder, in the case of a sample from whole blood, will contain red blood cells and other white blood cells. Alternatively, the composition can be formed as a density gradient prior to or during centrifugation.

In a preferred embodiment using differential cut-off density centrifugation, the sample of cells is mixed with a centrifugation medium such that the resulting density is intermediate between the buoyant density of the cell population of interest and other cell populations in the sample. For example, the density of the mixture is greater than the buoyant density of mononuclear cells and less than the buoyant density of red blood cells and granulocytes in a sample of whole blood. In this embodiment, the centrifugation mixture is subjected to centrifugation such that the mononuclear cells "float" to the meniscus in a relatively narrow band. Centrifugation of such a mixture for longer than such time, for example until isopycnic equilibrium is reached, will result in a broader band (or bands) of desired cells.

Differential cut-off centrifugation or other centrifugation procedures within the scope of the invention can be adapted without undue experimentation in light of the present specification for cells other than mononuclear cells from whole blood.

Generally, the final desired density of the centrifugation mixture is about 1.077 grams per milliliter of fluid to separate mononuclear cells. However, the density of the centrifugation medium and the mixture will vary according to the osmolarity, type and volume of the cells in the sample.

By "isotonic," it is meant that the mixture, once it is made, is approximately isotonic to the cells from the sample, such that the cells do not rupture pursuant to the effects of an osmotic difference. Generally, this isotonic state is achieved through the use of an osmotic agent, such as sucrose or an appropriate salt. An appropriate salt is a salt that does not otherwise interfere with the performance of the method; accordingly, a salt which effectively prohibits the amplification of the nucleic acids is not desirable. It is sometimes advantageous if the osmotic agent does not add to the ionic concentration in the mixture, e.g., such as when the osmotic agent is sucrose.

The centrifugation medium preferably is able to be used directly in the sample, such as blood, and does not lyse the cells in the sample. Some examples of useful centrifugation media include PERCOLL, SEPRACELL-MN, and NYCODENZ. Other useful media, including Ficoll-hypaque or Ficoll-isopaque, are typically used by layering rather than mixing. For example, if the centrifugation medium lyses white blood cells, then nucleic acid may be prematurely released. If red blood cells are lysed they release hemoglobin, and therefore a source of ferric ion, which interferes with the later amplification reactions. It is preferred that the centrifugation medium allow more than or equal to about 50% of mononuclear cells present in a sample of whole blood to be recovered after centrifugation.

Centrifugation

The mixture is then subjected to centrifugation such that the desired cells effectively move to form a discrete band of isolated cells. In the case of isopycnic centrifugation or centrifugation using centrifugation media intermediate the desired cell population and other cells in the sample, the desired cells effectively move toward the end of the centrifuge tube that is toward the center of rotation, rising to the top of the centrifugation medium to form an upper portion containing isolated cells, along with some platelets and/or lipids and other constituents.

In one example, the mixture is centrifuged at about 2,900 rpm for about 20 minutes (about 1,500×g). The centrifugation is gentle enough that the centrifugation does not cause a substantial part, or significant percentage, of the cells to lyse, which means that sufficiently few cells lyse that the amplification of nucleic acid recovered from intact cells may proceed.

The centrifugation may be performed in a centrifugation tube wherein the part of the tube near the discrete band (e.g., the part of the tube near the center of rotation in isopycnic centrifugation), is formed so as to accentuate that portion of the composition containing the desired cells, such as mononuclear cells. This may be done, for example, by narrowing the interior diameter of the tube. Further, the centrifugation may be performed using a device that will inhibit turbulence, and therefore mixing, while making the composition, while performing centrifugation, and/or while removing the isolated, desired cells. An example of such a device is a porous nylon filter that will allow desired cells to pass through it.

Removal of the Portion Containing the Desired Cells

After centrifugation, the portion of fluid containing the desired cells (the discrete band) can be removed from the rest of the mixture using any means known in the art, such as by suctioning the portion using a pipette. Generally, less than about 20% of the total original volume is removed, e.g., about 500 ul of 6 ml, and preferably only about the top 100 ul at or adjacent the meniscus.

Lysing the Desired Cells

After removing the isolated desired cells, the cells are lysed to release the nucleic acid from, or associated with, the cells. This means any nucleic acid either attached to or found within or on the desired cells.

The cells may be lysed by any desired method, including, for example, the use of a strong alkali, use of an enzymatic agent, use of a detergent, use of osmotic shock, use of chaotropic concentrations of solutes, or use of sonic disruption. In a preferred embodiment, the cells may be lysed by use of potassium hydroxide. This alkali, or an equivalent alkali, e.g., NaOH or LiOH, is particularly useful since it also inactivates cellular nucleases and thus prevents inhibition of later enzymatic reactions using the alkali-induced lysate, and may also denature double stranded nucleic acid.

Addition of A Chelating Agent

An agent that complexes with ferric ion and/or calcium ion and/or other undesirable ions may be added to the density centrifugation medium or to the solution during or after lysis. "Complexes" means that the agent effectively attaches itself to the ion, whether through chelation, coordination, covalent bonding or some other form of bonding or attachment, such that the ion may no longer prevent the later amplification reaction of the invention. These ions are removed from the solution resulting from the lysis because they may inhibit enzymes that may be used in other steps of the method, such as amplifying the nucleic acid from mononuclear cells.

Preferably, the complexing agent is a chelating agent that removes such ions from solution, but does not bind significantly with zinc ions nor magnesium ions, as these ions are helpful to some reagents that may be used in the later amplification reaction. See generally Zinc in DNA Replication and Transcription, Wu, F. Y. H., and Wu, C. W., Ann. Rev. Nutr. 7:251 (1987).

Examples of chelating agents that may be used are deferoxamine and transferrin. Deferoxamine has a $10^{31}$ binding constant for the ferric ion, see Antioxidant Capacity of Desferrioxamine and Ferrioxamine in the Chemically-Initiated Lipid Peroxidation of Rat Erythrocyte Ghost Membranes, Videla, C. A., et al., Biochem. Int'l, 16, 799 (May 1988), and binds preferentially to zinc and ferric ions magnesium ions. Deferoxamine has a $10^{11.1}$ binding constant for $Zn^{2+}$, and a $10^{4.3}$ binding constant for $Mg^{2+}$. Examples of calcium ion complexing agents are oxalate and citrate. Oxalate and citrate also bind $Fe^{+++}$ with greater stability compared to $Mg^{++}$, especially at neutral-alkaline pH. Other agents, such as EDTA, are not preferred chelating agents, as they bind zinc ion and magnesium ion, along with other divalent cations.

Some useful chelating agents may have the potential to bind desirable ions (e.g., $Mg^{++}$, $Zn^{++}$), but may be beneficial if they bind undesirable ions preferentially. For example, EGTA binds $Ca^{++}$ in preference to $Mg^{++}$. Thus, if the concentration of EGTA is less than the concentration of $Mg^{++}$, there will still be a desirable and predictable activity of free $Mg^{++}$ but trace levels of $Ca^{++}$ will be effectively sequestered. Furthermore, if such a chelator is mixed with a desirable species, such as $Mg^{++}$, prior to adding it to the reaction of interest, the free activity of $Mg^{++}$ contributed to the reaction from other sources will not be reduced by addition of the complexed chelator, but the chelator may effectively sequester preferentially bound species such as $Ca^{++}$, especially if the association/dissociation rates are relatively rapid.

The use of a chelating agent is particularly helpful when an anticoagulant has been used previously in the method, as the use of such an anticoagulant may cause or allow the release of ferric ions.

Later reactions, such as amplification, using the lysate may also be inhibited by a variety of polyanions. Provision of an effective amount of a polycation such as polyethyleneimine (PEI) can neutralize such polyanions. An effective amount of such a polycation is that amount necessary to reduce inhibition by a polyanion. It is surprising that a polycation such as PEI would have such a beneficial effect because nucleic acids themselves are densely charged anions.

Amplification of Nucleic Acid from Desired Cells

The nucleic acid may now be amplified using any method known in the art, such as a polymerase chain reaction procedure, or a procedure described by Kacian, supra, using RNAse H, reverse transcriptase and RNA polymerase. Preferably, the amplification will target the same sequence of nucleic acid that will be the target of the probe, discussed below. The nucleic acid amplification may be performed on the nucleic acid from the desired cells without first removing the debris from the centrifugation and lysis, nor otherwise "cleaning up" the portion containing the isolated desired cells, other than appropriately preparing the chemical balance of the solution to be subjected to amplification, for example, neutralizing the lysis agent such as potassium hydroxide.

Screening for Desired Nucleic Acid

The amplified nucleic acid is now ready to be screened for a desired sequence of nucleic acid using any procedure known in the art or other related procedures, such as hybridization using a strand of DNA or RNA complementary to the desired nucleic acid sequence, which complementary strand is known as a "probe." The probe may be hybridized to the nucleic acid and detected using any known detection technique, such as traditional Southern or Northern blotting techniques, or the homogeneous protection assay ("HPA") described by Arnold et al., supra. In a preferred embodiment, the probe will detect the nucleic acid associated with an HIV virus.

Kit for Effecting the Above Method

A simple kit for performing the above method may be prepared from readily available materials and reagents. The kit may be designed so that the reagents complement each other, for example, the osmotic agent may be sucrose and the centrifugation medium PERCOLL®.

EXAMPLES

Preparing Density Centrifugation Medium

PERCOLL® is provided by the manufacturer at a density in the range 1.130±0.005 g/ml. The precise density is supplied with each lot. To make a 1 liter (1000 ml) suspension of PERCOLL® in 0.25M sucrose at a specified density, $\rho_{Desired}$, the volume (in ml) of PERCOLL® stock required can be estimated from the following equations:

$$\rho_{Desired} = \frac{V_{Percoll}\rho_{Percoll} + V_{Osmot}\rho_{Osmot} + (1000 - V_{Percoll} - V_{Osmot})}{1000 \text{ ml}}$$

or, $$V_{Percoll} = \frac{1000(\rho_{Desired} - 1) - V_{Osmot}(\rho_{Osmot} - 1)}{(\rho_{Percoll} - 1)}$$

In this example, sucrose is the osmoticum and is introduced into the mixture as a 5× (1.25M) stock; thus for a final concentration of 0.25M, the volume ($V_{Osmot}$) to be added= 200.0 ml. The density of 1.25M sucrose is 1.1607 g/ml. The final term in the numerator of the first equation (1000– $V_{Osmot}$–$V_{PERCOLL®}$) represents the volume of water added to bring the final volume up to one liter and assumes a nominal density of 1.000 g/ml for water. Thus, 1.) To make a suspension with a density of 1.110 g/ml using a stock solution of PERCOLL® supplied at a density of 1.131 g/ml, mix:
594.4 ml PERCOLL®
200.0 ml 1.25M Sucrose
205.6 ml H$_2$O 2.) Accurately measure the refractive index (RI) of the resulting suspension. Calculate the density using the relationship (described by Pharmacia) appropriate for density centrifugation medium (DCM) comprising PERCOLL® in 0.25M sucrose (DCM$_1$):

$$\rho_{DCM_1} = (6.6145 \times RI_{DCM_1}) - 7.8620$$

The RI expected for the desired 1.110 g/ml suspension would thus be 1.3564.

3.) If the desired density is difficult to obtain, or sufficiently accurate volumetric glassware is not available, use the formula above as a guide to estimate volumes required to make 2 suspensions with densities which bracket the desired final density (e.g., 1.105 g/ml and 1.115 g/ml). Measure the RI of each and calculate the true density of each. Calculate the volumes of each to mix (e.g., $V_{low}$ and $V_{high}(=V_{Tot}-V_{low})$) to obtain the desired density and total volume:

$$\rho_{Desired} = \frac{\rho_{low}V_{low} + \rho_{high}(V_{Tot} - V_{low})}{V_{Tot}}$$

4.) A similar strategy can be used for making PERCOLL® suspensions in other osmotica such as 0.15M NaCl. The density of NaCl solutions is also available in the literature and can be calculated as a function of concentration. For example, 1.50M NaCl, which can be used as a 10× stock instead of the 5× sucrose in the formulation above, has a density of 1.058 g/ml. The density can be calculated from the RI of such a PERCOLL®/saline DCM$_2$ by the following equation:

$$\rho_{DCM_2} = (6.8166 \times RI_{DCM_2}) - 8.0923$$

A refractive index of 1.350 would correspond to the desired density of 1.110 g/ml for DCM$_2$.

5.) Agents other than PERCOLL® can be used to generate the desired density. (As outlined in the Pharmacia and Nycomed product literature, the desired properties of a density reagent include: sufficient solubility and specific gravity to yield solutions of at least the desired density, little osmotic activity of its own, and low viscosity in solution.) For example, NYCODENZ® stock solutions can be made by dissolving it in water at a density greater than desired as the final DCM density (e.g. >0.35M). The density of an aqueous NYCODENZ® solution can be predicted from its molarity:

$$\rho_{Nycodenz} = (0.43914[\text{Nycodenz}]) + 0.99828$$

and confirmed by its RI:

$$\rho_{Nycodenz} = (3.242 \times RI_{Nycodenz}) - 3.323$$

Such a NYCODENZ® stock solution of known density can be used in conjunction with a suitable osmoticum to yield an iso-osmotic DCM of the desired density using the same procedure described for PERCOLL® above. The densities of the resulting mixtures can be calculated from the refractive indices using the following constants (from Nycomed):

$$\rho_{DCM_3} = (3.553 \times RI_{DCM_3}) - 3.751$$

for NYCODENZ® in sucrose ($DCM_3$), and:

$$\rho_{DCM_4} = (3.287 \times RI_{DCM_4}) - 3.383$$

for NYCODENZ® in saline ($DCM_4$).

The buoyant density of the cells present in the sample, such as blood, can change if the osmotic strength is changed. Typically, the buoyant density of the cells decreases as the osmolarity is decreased and increases as the osmolarity is increased. While various combinations of osmolarity and medium density can be used to achieve similar results, the near-physiological osmolarities described here are suited to the purpose of this method (preparing cells for subsequent amplification reactions). Further, Red Blood Cells (RBCs) are typically more sensitive to osmotic shock than White Blood Cells (WBCs) and the most suitable sample processing conditions are those which minimize the possibility of RBC lysis.

As described herein, a density of 1.110 g/ml is preferred for the DCM to mix with whole blood in order to obtain a final mixture density of 1.077 g/ml to separate mononuclear cells from whole blood. This density for the DCM was chosen empirically based on the results of several experiments including examinations of the number of cells recovered, of the purity of the desired fraction, i.e. low granulocyte contamination as determined by Wright staining, and by observing a typical ratio of lymphocytes-to-monocytes, as determined by Wright staining, among the cells recovered. This DCM density is also a preferable density based on the typical buoyant density of mononuclear cells (usually considered to be <1.077 g/ml) and the normal range of blood composition. The packed volume of RBCs for most adult individuals is usually at least 35% of the total blood volume, although this can be lower for individuals with significant anemia. When the DCM and whole blood are mixed, the density of the resulting liquid phase should be a combination of the partial volumes contributed from each source, i.e., the DCM and plasma, and their respective densities:

$$\rho_{Plasma/DCM} = \frac{V_{DCM}\rho_{DCM} + V_{Plasma}\rho_{Plasma}}{V_{DCM} + V_{Plasma}}$$

If equal volumes of DCM, with a density=1.110 g/ml, and blood are mixed and if 65% of the blood volume is plasma, with a density of 1.026 g/ml, then the density of the resulting liquid phase will be 1.077 g/ml, which is an ideal density for separating mononuclear cells from other blood cells. In such a mixture, most of the mononuclear cells will float to the top of the mixture, along with many of the platelets; the RBCs and granulocytes will sediment. Using this approach, it is apparent that the preferred density will vary according to conditions within the blood cell sample (such as blood) and the DCM. Determining an appropriate density using the above mentioned factors does not require undue experimentation.

Figure 1:
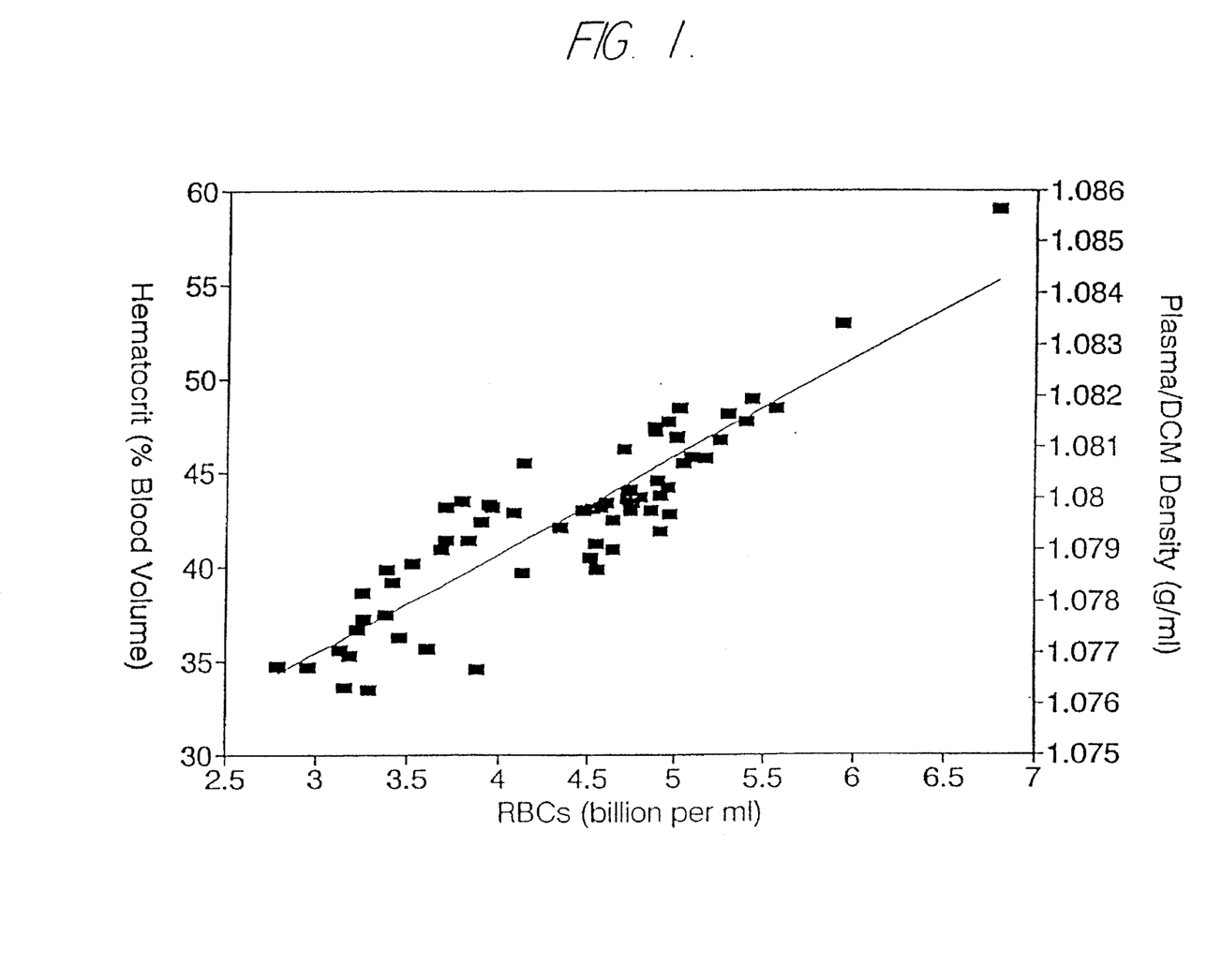
FIG. 1 is a graph depicting the red blood cell counts, hematocrits, and plasma density for 66 different individuals.

Blood from the majority of individuals will have a packed RBC volume (as measured by hematocrit procedures) greater than 35% of the total blood volume. Thus mixing equal volumes of blood and 1.110 g/ml DCM will yield a liquid phase with a density>1.077 g/ml for most blood samples. The target mononuclear cell fraction will float even more readily to the top of such a mixture. FIG. 1 shows the RBC counts and hematocrits determined for blood taken from 66 different individuals. The $2^{nd}$ y-axis shows the corresponding density of the DCM-plasma mixture which would result from mixing a specified volume of DCM with an equal volume of blood having the hematocrit directly opposite on the primary y-axis. The example shows that the strategy described here would result in DCM/plasma mixture having a density between 1.076 g/ml–1.082 g/ml for the majority of individuals. As the density of the mixture increases, some granulocyte contamination might be expected among the mononuclear cell (MNC) fraction. However, mixtures throughout this density range should be very effective at separating MNC and granulocytes since the buoyant density of the granulocytes typically averages 1.086 g/ml and only a small fraction have a buoyant density <1.082 g/ml. Moreover, for some aspects of the invention, such as nucleic acid target amplification and/or hybridization analysis, even substantial granulocyte contamination is not a significant problem since these techniques have been designed to be specific for desired target sequences even in the presence of vast excess levels of non-target sequences. For example, while it is advantageous to recover a cell population which is highly enriched in MNC, which include target cells for HIV infection, over granulocytes, which are not target cells for HIV infection, it is not absolutely required. It is more important in such a case to use conditions which result in recovering most of the MNC than to recover highly purified MNC.

Using the procedures described above it has been possible to make DCM of the desired density±0.002 g/ml reproducibly and reliably.

It should be noted that the invention does not require that the blood and DCM be combined in equal volumes or that the DCM density is constrained to be 1.110 g/ml. It is within the skill of the art without undue experimentation to calculate the appropriate volumes to combine for a wide range of DCM densities based on the partial volumes of the components and their respective densities as described above. Conversely, the appropriate DCM density to use can be calculated to accommodate the desired volume and ultimate mixture density specifications.

Example of Blood Fractionation to Recover Mononuclear Cells

1.) Mix 3.0 ml EDTA anti-coagulated whole blood with 3.0 ml isosmotic PERCOLL®/sucrose DCM (density=1.110 g/ml) in a screw cap test tube. Cap securely and invert several times to mix thoroughly.

2.) Centrifuge in swinging bucket rotor at 1600×g for 20 min. RBCs will pellet. Granulocytes will pellet with, and band on top of, the RBCs. MNC will float to the top of the mixture. Other centrifugation conditions may be used. For example, greater g-force can be used for a shorter time, but it is preferred that g-force not exceed a level where full isopycnic equilibrium is attained, as the MNC may then band below the meniscus. Geometry of the tube may also affect centrifugation time and force. For example, a shorter column of liquid should reach isopycnic equilibrium more quickly. Further, devices to stabilize the meniscus and/or MNC band may be used. Adapting the centrifugation conditions appropriately for such differing conditions, or for different cell types or sample sources, does not require undue experimentation for one of skill in the art. Also, the invention may include a centrifugation procedure comprising at least one wash step. Such methods are known in the art. The appearance of the MNC band will vary slightly depending on the specifics of the centrifugation and the centrifugation apparatus, such as the diameter of the tube, volume of blood used, etc., but will typically concentrate at the highest point of the meniscus.

3.) The complete MNC band may be harvested by aspirating into a pipet, manipulating the pipet so that the tip remains in a region of dense cell accumulation. Continue until most of the MNC are recovered. Typically, this will result in collection of 300–700 μl of the MNC/DCM/plasma suspension.

Example of Cell Lysis Method for Mononuclear Cells

1.) Mix 250 μl of the MNC suspension with 250 μl 0.14N KOH. Vortex to mix well. Heat at 95° C. for 30 min.

2.) Adjust the pH of the resulting hydrolysate to pH 8.0±0.5 (typically) by adding 50 μl of a solution comprising:

0.65N Acetic acid (HOAc)

0.066M Tris(hydroxymethyl amino)methane, base 0.084M Tris•HCl

3.) Mix well, e.g., by vortexing.

Other methods to cause lysis may also be used, for example, combinations of other basic solutions followed by neutralizing acid solutions, or enzymatic or mild detergent agents. Such methods, for mononuclear cells and for other cells, are known in the art.

Using the Lysate in Amplification Reactions

The above lysate contains a crude mixture of biologically derived molecules, many of which are low molecular weight hydrolysis products of the original sample constituents. The DNA present in these lysates, while fragmented and denatured compared to its original structure within the cells, is still a suitable reactant for a variety of chemical and biochemical reactions, including as a template for nucleic acid target amplification. To minimize the complexity and manipulations involved in practical, routine use of target amplification to analyze blood-derived nucleic acids, in one aspect of the invention the lysate is added directly to the amplification reaction as the source of the analyte, without further purification. However, it is well known that biologically-derived samples frequently contain components that are inhibitory to in vitro biochemical reactions, including enzyme reactions. For example, even nucleic acid preparations that are much more highly purified than the lysate yielded by the method described herein have been reported to contain potent inhibitors of polymerase chain reaction amplification (R. deFranchis, N. C. P. Cross, N. S. Foulkes and T. M. Cox, A Potent Inhibitor of Taq Polymerase Copurifies with Human DNA, Nucleic Acids Research 16:10355 (1988)).

Many metal ions, especially polyvalent species, can inhibit enzyme activities through a variety of mechanisms, including displacement or substitution of requisite metal co-factors, or by forming stable complexes with susceptible moieties, including amino acid side chains which are necessary for catalytic activity or which result in deleterious steric changes in the enzyme or by promoting deleterious redox reactions. Chelators are sometimes employed to sequester undesirable metals but it is not obvious in any particular case that an efficacious chelator can be identified which does not itself inhibit the enzyme activity, e.g., by complexing necessary co-factors or even stripping bound metals from the enzyme. Deferoxamine, a biologically-derived natural product with extremely high affinity for Fe(III), was found to be highly effective at neutralizing the inhibition imposed by lysates of blood fractions on the amplification reactions and was found to be well tolerated in the reaction over at least the concentration range of 0.001–1 mM. An example of deferoxamine's use is described below and the beneficial effects demonstrated in FIGS. 2 and 3.

Figure 2:
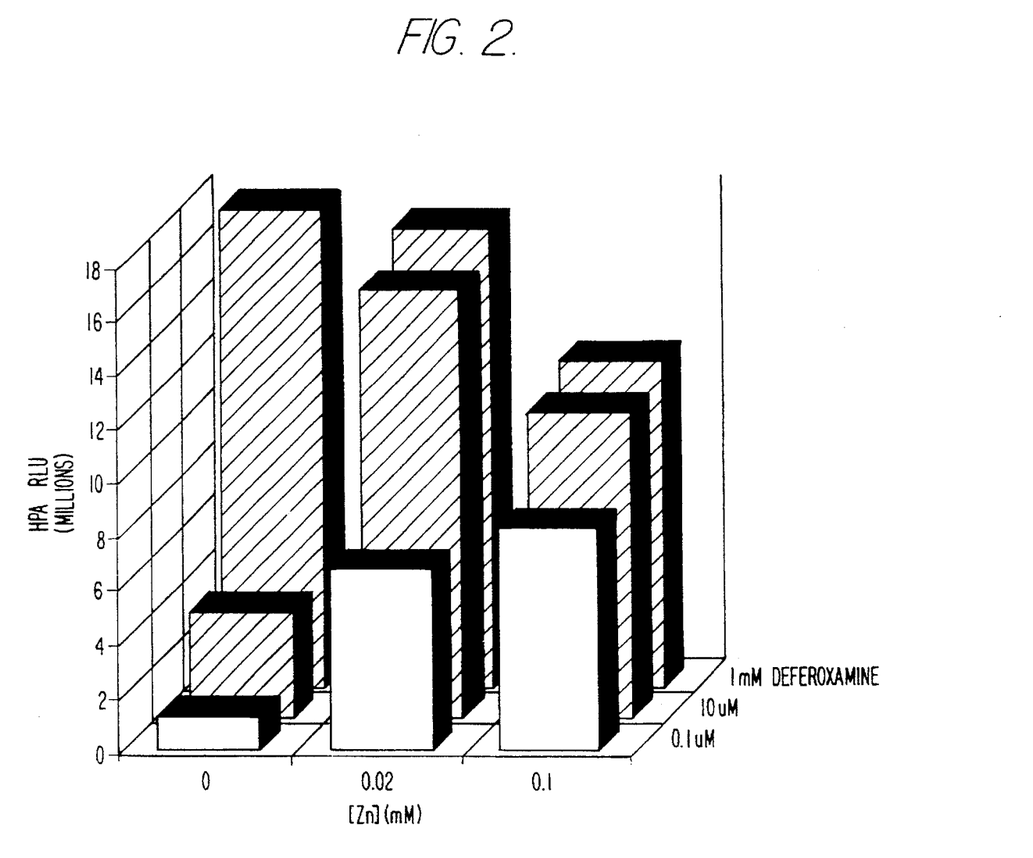
FIG. 2 is a chart depicting the effects on amplification of zinc titration in concert with deferoxamine.

One of the agents tested and found to be effective at counteracting the lysate sample inhibition of amplification was $Zn(OAc)_2$. Although reverse transcriptase has been reported to be a Zn metalloenzyme (as has T7 RNA polymerase, though this is no longer thought to be the case) it is not known if (or claimed that) the beneficial activity of $Zn^{++}$ in this context is related to the normal $Zn^{++}$ binding site of one or more enzymes in the reaction. It is possible that $Zn^{++}$ interacts with other site(s) on the enzyme(s) in a favorable way or that it interferes directly or indirectly with one of the inhibitors in reactions of this type. It was not obvious that conditions could be identified where net beneficial effects were observed. FIG. 2 shows an example of the enhancement possible from $Zn^{++}$ in the amplification reaction, especially at negligible deferoxamine levels. While the deferoxamine benefits may be slightly antagonized by high $Zn^{++}$ levels, it is apparent that mixtures can be identified over fairly broad concentration ranges of each which support a stable platform of effective amplification.

Figure 3:
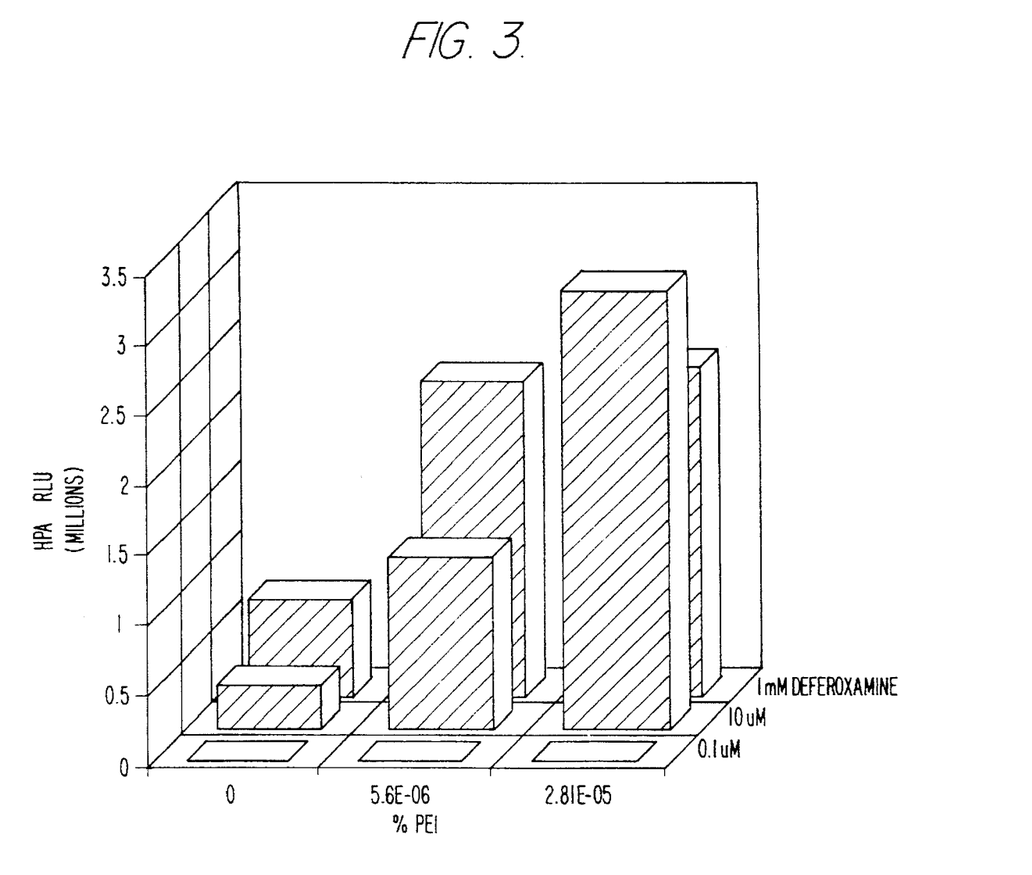
FIG. 3 is a chart depicting the effects of polyethyleneimine (PEI) and deferoxamine on amplification.

Many nucleic acid reactive enzymes are inhibited by a variety of polyanions. One strategy for neutralizing polyanions is to include a polycationic species such as polyethyleneimine (PEI) in the reaction. Since nucleic acids are themselves densely charged anions, it was surprising that conditions could be identified under which enhanced amplification could be observed without detectable loss of endogenous template activity. PEI concentrations of $<3\times10^{-5}\%$ (w/v) in the amplification reaction have been consistently beneficial in these respects. An example of the enhancement possible is shown in FIG. 3.

The example described below illustrates execution of an amplification that might contain one or more of these anti-inhibitory compounds.

1.) Prepare and dispense 40 μl of a solution containing the following components. The concentrations listed refer to the respective concentrations in the completed 100 μl reaction.

50 mM Tris•HCl (pH 8.0 at room temperature)

17.5 mM $MgCl_2$ 5 mM DTT 2 mM Spermidine 6.25 mM ea GTP & ATP 2.5 mM ea UTP & CTP 0.2 mM ea dATP, dGTP, dCTP, dTTP 0.3 mM ea primer "A" & primer "B"

2.) Optionally, include Deferoxamine mesylate at 0–1 mM final concentration. Optionally, include $Zn(OAc)_2$ at 0–0.1 mM final concentration. Optionally, include PEI at $0-3\times10^{-5}\%$ final concentration.

3.) Add to this mixture, 40 μl of the hydrolyzed MNC suspension prepared as described above. Optionally add a known amount of purified nucleic acid containing the target sequence(s) of interest as a basis for comparing amplification performance supported by different conditions.

4.) Heat the mixture to 95° C. and maintain for 5 minutes. Cool the mixture to 37° C.

5.) Add 10 μl of a solution containing 600 U Moloney MuLV reverse transcriptase (MMLV-RT), preferably in a buffered solution of composition sufficient to maintain enzyme stability during handling. Incubate the mixture for 10–15 minutes at 37° C.

6.) Heat the mixture to 95° C. and maintain at this temperature for 5 minutes. Then cool the mixture to 37° C.

7.) Add 10 μl of a solution containing 600 U MMLV-RT and 400 U T7 RNA polymerase, preferably in a buffered solution of composition sufficient to maintain enzyme stability during handling.

8.) Mix briefly and incubate the mixture at 37° C. for 1–2 hours.

9.) Determine the amount of amplification product formed as a copy of the intended target sequence using a specific hybridization procedure such as the hybridization protection assay. See, e.g., Arnold et al., supra.

Other forms of deferoxamine may also be used, as well as other zinc providers, such as $ZnCl_2$ or $ZnSO_4$. Also, other polycationic polymers such as polyallyl amine or Polybrene® (hexadimethrine bromide) may also be used with or instead of PEI.

The present embodiments of this invention are to be considered in all respects as illustrative and not restrictive, the scope of the invention being indicated by the appended claims rather than by the foregoing description, and all changes which come within the meaning and range of equivalency of the claims therefore are intended to be embraced therein.

What is claimed is:

1. A method of preparing and amplifying nucleic acid, said method comprising the steps of:

a) centrifuging a composition comprising a centrifugation medium and a sample of blood cells comprising mononuclear cells, under centrifugation conditions such that a substantial portion of said mononuclear cells in said composition gather in a discrete band;

b) separating said discrete band from said composition;

c) lysing said mononuclear cells in said discrete band by
      i) providing to said band a lysing agent, or
      ii) exposing said band to sonic disruption,
   so that said mononuclear cells in said band lyse, thereby rendering said nucleic acid available for amplification;

d) providing to said band a first complexing agent able to complex ferric ions, wherein said first complexing agent is selected from the group consisting of deferoxamine, sideramine, sideramycin and ferrimycin; and e) amplifying said nucleic acid.

2. The method of claim 1, wherein said first complexing agent is deferoxamine.

3. The method of claim 1 further comprising providing to said band a second complexing agent able to complex calcium ions.

4. The method of claim 3, wherein said second complexing agent is EGTA, citrate or oxalate.

5. The method of claim 3, wherein said first and second complexing agents are the same complexing agent.

6. The method of claim 3, wherein said first and second complexing agents have a greater affinity for undesirable ions than for desirable ions.

7. The method of claim 6, wherein said desirable ions include at least one of zinc, manganese and magnesium ions.

8. The method of claim 7, wherein at least one of said first and second complexing agents is provided to said band as a complex or salt, and wherein said complex or salt comprises said complexing agent and at least one of said desirable ions.

9. The method of claim 1, wherein zinc ions are provided to said band during at least one of said providing, exposing, and amplifying steps.

10. The method of claim 1, wherein said composition is isotonic with said mononuclear cells, such that said composition lyses less than 20% of said mononuclear cells present in said composition prior to said lysing step.

11. The method of claim 1, wherein said composition is mixed prior to said centrifuging step.

12. The method of claim 1, wherein said band is adjacent to the meniscus of said composition.

13. The method of claim 1, wherein said centrifugation medium is isopycnic to said blood cells.

14. The method of claim 1, wherein said band comprises at least 30% of said mononuclear cells present in said composition.

15. The method of claim 1, wherein said band comprises 20% or less of the total volume of said composition.

16. The method of claim 1, wherein said band comprises 10% or less of the total volume of said composition.

17. The method of claim 1, wherein said band further comprises platelets.

18. The method of claims 1, wherein said centrifugation medium contains an osmotic agent isotonic to said mononuclear cells, wherein said osmotic agent comprises sucrose, sorbitol, mannitol, sodium chloride, or sodium glutamate.

19. The method of claim 18, wherein said osmotic agent does not alter the ionic concentration of said composition.

20. The method of claim 1, wherein said centrifugation conditions include centrifuging at about 1600×g.

21. The method of claim 1, wherein said centrifugation medium comprises colloidal silica or colloidal silica coated with polyvinyl pyrrolidone.

22. The method of claim 1, wherein said centrifugation medium is prepared with a compound having iodinated benzoic acid derivatives.

23. The method of claim 1, wherein said blood cells are derived from whole blood or animal serum.

24. The method of claim 1, wherein at least 80% of said blood cells in said sample remain intact after said separating step and prior to said lysing step.

25. The method of claim 1, wherein said amplifying step is conducted using polymerase chain reaction amplification.

26. The method of claim 1, wherein said amplifying step is conducted in the presence of reverse transcriptase and RNA polymerases.

27. The method of claim 1, wherein said lysing agent is an alkali, an enzyme, or a detergent.

28. The method of claim 1, wherein said lysing agent is KOH, $(CH_3)_4NOH$, NaOH, or LiOH.

29. The method of claim 1, wherein said sample of blood cells is contacted with an anticoagulant before said centrifuging step.

30. The method of claim 29, wherein said anticoagulant comprises EDTA, citrate, oxalate or heparin.

31. The method of claim 1, wherein said centrifugation medium has a density of between 1.105 and 1.115 grams per milliliter.

32. The method of claim 1, whereto said separating step is conducted with a device that inhibits mixing of said band and said composition.

33. The method of claim 1, wherein said centrifuging step is conducted in a tube altered to enhance separation of said band from said composition.

34. The method of claim 1, wherein said amplifying step further includes a polycationic polymer in an amount effective to reduce inhibition by a polyanion.

35. The method of claim 1, wherein said band is contacted with said first complexing agent after said lysing step and before said amplifying step.

36. The method of claim 1, wherein said nucleic acid is from a human immunodeficiency virus or hepatitis B virus contained in said mononuclear cells.

37. A method of amplifying nucleic acid in an amplification mixture, said method comprising the steps of:
   a) providing to said mixture a first complexing agent selected from the group consisting of deferoxamine, sideramine, sideramycin and ferrimycin, so that said amplifying in the presence of said first complexing agent yields more amplified nucleic acid than amplifying in the absence of said first complexing agent; and
   b) amplifying said nucleic acid in the presence of said first complexing agent.

38. The method of claim 37, wherein said first complexing agent is deferoxamine.

39. The method of claim 37 further comprising the steps of:
   providing to said mixture a second complexing agent able to complex calcium ions, so that said amplifying in the presence of said second complexing agent yields more amplified nucleic acid than amplifying in the absence of said second complexing agent; and
   amplifying said nucleic acid in the presence of said second complexing agent.

40. The method of claim 39, wherein said second complexing agent is EGTA, citrate or oxalate.

41. The method of claim 39, wherein said first and second complexing agents are the same complexing agent.

42. The method of claim 39, wherein said first and second complexing agents have a greater affinity for undesirable ions than for desirable ions.

43. The method of claim 42, wherein said desirable ions include at least one of zinc, manganese, or magnesium ions.

44. The method of claim 43, wherein at least one of said first and second complexing agents is provided to said band as a complex or salt, wherein said complex or salt comprises said complexing agent and at least one of said desirable ions.

45. The method of claim 37 or 39 further comprising providing zinc ions to said mixture.

46. A method of amplifying a sample of nucleic acid, said method comprising the steps of:
   a) providing to said sample of nucleic acid:
      i) a first complexing agent able to complex ferric ions, so that said amplifying in the presence of said first complexing agent yields more amplified nucleic acid than amplifying in the absence of said first complexing agent;
      ii) zinc ions to facilitate said amplifying; and
   b) amplifying said nucleic acid in the presence of said first complexing agent and said zinc ions.

47. The method of claim 46, wherein said first complexing agent is deferoxamine, sideramine, sideramycin, or ferrimycin.

48. The method of claim 47, wherein said first complexing agent is deferoxamine.

49. The method of claim 46 further including providing a second complexing agent able to complex calcium ions.

50. The method of claim 49, wherein said first and second complexing agents are the same complexing agent.

51. The method of claim 49, wherein said second complexing agent comprises EGTA, citrate, or oxalate.

52. A method of amplifying a sample of nucleic acid, said method comprising the steps of:
   a) providing to said sample of nucleic acid:
      i) a first complexing agent able to complex ferric ions, so that said amplifying in the presence of said first complexing agent yields more amplified nucleic acid than amplifying in the absence of said first complexing agent;
      ii) a polycationic polymer in an amount effective to reduce inhibition by a polyanion; and
   b) amplifying said nucleic acid in the presence of said first complexing agent and said polycationic polymer.

53. The method of claim 52, wherein said first complexing agent is deferoxamine, sideramine, sideramycin or ferrimycin.

54. The method of claim 52, wherein said first complexing agent is deferoxamine.

55. The method of claim 52, further comprising providing to said sample a second complexing agent able to complex calcium ions.

56. The method of claim 55, wherein said second complexing agent comprises EGTA, citrate, or oxalate.

57. The method of claim 55, wherein said first and second complexing agents are the same complexing agent.

58. The method of claim 52, wherein said polycationic polymer is polyethyleneimine, polyallylamine, or hexadimethrine bromide.

59. A method of preparing nucleic acid from mononuclear cells, said method comprising the steps of:
   a) centrifuging a composition comprising a centrifugation medium and mononuclear cells under centrifugation conditions such that at least about 30% of said mononuclear cells gather in a discrete band;
   b) separating said band from said composition;
   c) providing to said band a lysing agent so that said mononuclear cells present in said band lyse; and
   d) providing to said band a first complexing agent able to complex ferric ions, wherein said first complexing agent is selected from the group consisting of deferoxamine, sideramine, sideramycin and ferrimycin.

60. The method of claim 59, wherein said first complexing agent is deferoxamine.

61. The method of claim 59, further comprising providing to said band a second complexing agent able to complex calcium ions.

62. The method of claim 61, wherein said second complexing agent is EGTA, citrate, or oxalate.

63. The method of claim 61, wherein said first and second complexing agents are the same complexing agent.

64. The method of claim 59, wherein said separating step is conducted with a device that inhibits mixing of said band and said composition.

65. The method of claim 59, wherein said centrifuging is conducted in a tube that enhances separation of said band from said composition.

66. The method of claim 59, wherein said band comprises at least 50% of said mononuclear cells present in said composition.

67. The method of claim 59, wherein at least one of said providing steps further includes a polycationic polymer in an amount effective to reduce inhibition by a polyanion.

68. The method of claim 67, wherein said polycationic polymer is polyethyleneimine, polyallylamine or hexadimethrine bromide.

69. The method of claim 59, wherein said cells are provided in whole blood.

70. The method of claim 69, wherein said whole blood comprises human blood.

71. The method of claim 59, wherein said composition is mixed before said centrifuging step.

72. The method of claim 59, further including amplifying said nucleic acid after providing said first complexing agent.

73. The method of claim 59 or 72 wherein said nucleic acid is screened for a specific nucleic acid sequence.

74. A method of screening for the presence of a virus associated with a mononuclear cell, said method comprising the steps of:
   a) centrifuging a composition comprising a centrifugation medium and a sample of blood cells comprising mononuclear cells, under centrifugation conditions such that at least 30% of said mononuclear cells gather in a discrete band;
   b) separating said band from said composition;
   c) providing to said band:
      i) a lysing agent so that said mononuclear cells lyse, thereby rendering nucleic acid of said virus available for amplification;
      ii) a first chelating agent able to chelate ferric ions; and
      iii) a polycationic polymer in an amount effective to reduce inhibition by a polyanion; and
   d) amplifying said nucleic acid.

75. The method of claim 74, wherein said first chelating agent is deferoxamine, sideramine, sideramycin or ferrimycin.

76. The method of claim 74, wherein said first chelating agent is deferoxamine.

77. The method of claim 74, further comprising providing to said band a second chelating agent able to chelate calcium ions.

78. The method of claim 77, wherein said second chelating agent is EGTA, citrate or oxalate.

79. The method of claim 77, wherein said first and second chelating agents are the same chelating agent.

80. The method of claim 74, wherein said centrifugation medium is isopycnic to said blood cells.

81. The method of claim 74, wherein said band comprises 20% or less of the total volume of said composition.

82. The method of claim 74, wherein said lysing agent is KOH.

83. The method of claim 74, wherein said amplifying step is conducted in the presence of reverse transcriptase and RNA polymerases.

84. The method of claim 74, wherein said virus is a human immunodeficiency virus.

85. A kit for preparing nucleic acid for amplification, wherein said nucleic acid is derived from a sample of whole blood, said kit comprising a first complexing agent able to complex ferric ions, wherein said first complexing agent is deferoxamine, sideramine, sideramycin or ferrimycin; and amplification materials sufficient to amplify said nucleic acid.

86. The kit of claim 85, wherein said first complexing agent is deferoxamine.

87. The kit of claim 85, further comprising a second completing agent able to complex calcium ions.

88. The kit of claim 87, wherein said second complexing agent is EGTA, oxalate or citrate.

89. The kit of claim 87, wherein said first and second complexing agents are the same complexing agent.

90. The kit of claim 85, further comprising a centrifugation medium selected to have a density such that at least 30% of mononuclear cells in a composition comprising said medium and a sample of blood cells containing said mononuclear cells gather in a discrete band under centrifugation conditions.

91. The kit of claim 90, further comprising an osmotic agent in an amount sufficient to render said medium substantially isotonic to said whole blood.

92. The kit of claim 85, wherein said amplification materials are sufficient to amplify said nucleic acid using polymerase chain reaction amplification.

93. The kit of claim 85, wherein said amplification materials include reverse transcriptase and RNA polymerase.

94. The kit of claim 85, further comprising a lysing agent able to lyse mononuclear cells.

95. The kit of claim 94, wherein said lysing agent is KOH, $(CH_3)_4NOH$, NaOH or LiOH.

96. The kit of claim 85, further comprising a polycationic polymer in an mount effective to reduce inhibition by a polyanion.

97. The kit of claim 96, wherein said polycationic polymer is polyethyleneimine, polyallylamine or hexadimethrine bromide.

98. The kit of claim 85, further comprising a nucleic acid probe able to screen for said nucleic acid.

99. The kit of claim 98, wherein said nucleic acid is from a human immunodeficiency virus contained in mononuclear cells derived from a sample of human whole blood cells.

100. The kit of claim 98, wherein said nucleic acid is from a hepatitis B virus contained in mononuclear cells derived from a sample of human whole blood cells.

101. The kit of claim 85, further comprising a device for collecting and storing said whole blood.

102. A kit for amplifying a sample of nucleic acid, said kit comprising:
   a) a first complexing agent able to complex ferric ions, so that said amplifying in the presence of said first complexing agent yields more amplified nucleic acid than amplifying in the absence of said first complexing agent; and
   b) zinc ions to facilitate said amplifying.

103. The method of claim 102, wherein said first complexing agent is deferoxamine, sideramine, sideramycin or ferrimycin.

104. The method of claim 103, wherein said first complexing agent is deferoxamine.

105. The method of claim 102 further comprising a second complexing agent able to complex calcium ions.

106. The method of claim 105, wherein said second complexing agent is EGTA, citrate or oxalate.

107. The method of claim 105, wherein said first and second complexing agents are the same complexing agent.

108. A kit for amplifying a sample of nucleic acid, said kit comprising:
   a) a first complexing agent able to complex ferric ions, so that said amplification in the presence of said first complexing agent yields more amplified nucleic acid than amplifying in the absence of said first complexing agent; and
   b) a polycationic polymer in an amount effective to reduce inhibition by a polyanion.

109. The kit of claim 108, wherein said first complexing agent is deferoxamine, sideramine, sideramycin or ferrimycin.

110. The kit of claim 108, wherein said first complexing agent is deferoxamine.

111. The kit of claim 108, further comprising a second complexing agent able to complex calcium ions.

112. The kit of claim 111, wherein said second complexing agent is EGTA, oxalate or citrate.

113. The kit of claim 111, wherein said first and second complexing agents are the same complexing agent.

114. The kit of claim 108, wherein said polycationic polymer is polyethyleneimine, polyallylamine or hexadimethrine bromide.

115. A kit for screening for a virus that may be present in a sample of whole blood, said kit comprising:
   a) a centrifugation medium selected to have a density such that at least about 20% of mononuclear cells in a composition comprising said medium and said whole blood gather in a discrete band in said composition under centrifugation conditions;
   b) a lysing agent able to lyse said mononuclear cells, thereby rendering nucleic acid from said virus available for amplification;
   c) a first complexing agent able to complex ferric ions, wherein said first complexing agent is deferoxamine, sideramine, sideramycin or ferrimycin; and
   d) amplification materials sufficient to amplify said nucleic acid.

116. The kit of claim 115, wherein said first complexing agent is deferoxamine.

117. The kit of claim 115, further comprising a second complexing agent able to complex calcium ions.

118. The kit of claim 117, wherein said second complexing agent is EGTA, oxalate or citrate.

119. The kit or claim 117, wherein said first and second complexing agents are the same complexing agent.

120. The kit of claim 115, further comprising an osmotic agent in an amount sufficient to render said medium substantially isotonic to said whole blood.

121. The kit of claim 115, wherein said amplification materials are sufficient to amplify said nucleic acid using polymerase chain reaction amplification.

122. The kit of claim 121, wherein said amplification materials include reverse transcriptase and RNA polymerases.

123. The kit of claim 115, wherein said lysing agent is KOH, $(CH_3)_4NOH$, NaOH or LiOH.

124. The kit of claim 115 further comprising a polycationic polymer in an amount effective to reduce inhibition by a polyanion.

125. The kit of claim 124, wherein said polycationic polymer is polyethyleneimine, polyallylamine or hexadimethrine bromide.

126. The kit of claim 115 further comprising a nucleic acid probe able to screen for said nucleic acid.

127. The kit of claim 126, wherein said nucleic acid is from a human immunodeficiency virus contained in mononuclear cells derived from a sample of human whole blood cells.

128. The kit or claim 126, wherein said nucleic acid is from a hepatitis B virus contained in mononuclear cells derived from a sample of human whole blood.

129. The kit of claim 115 further comprising a device for collecting and storing said whole blood.

* * * * *